United States Patent [19]

Landa

[11] 4,285,596
[45] Aug. 25, 1981

[54] HOLOGRAPHIC DIFFRACTION GRATING SYSTEM FOR RAPID SCAN SPECTRAL ANALYSIS

[75] Inventor: Isaac J. Landa, Wheaton, Md.

[73] Assignee: Neotec Corporation, Silver Spring, Md.

[21] Appl. No.: 825,155

[22] Filed: Aug. 16, 1977

[51] Int. Cl.$^3$ ............................................. G01J 3/06
[52] U.S. Cl. .................................. 356/308; 356/328; 356/334
[58] Field of Search ............. 350/315, 266, 318, 3.86, 350/162 ZP, 162 R, 168, 172; 356/188, 189, 195, 205, 212, 244, 186, 51, 201, 96, 83, 84, 100, 51, 209, 328; 250/236, 340, 339; 362/35, 341, 347

[56] References Cited

U.S. PATENT DOCUMENTS

| | | | |
|---|---|---|---|
| 2,602,368 | 9/1950 | Barnes | 356/308 |
| 2,679,013 | 5/1954 | Barnes | 307/106 |
| 3,216,313 | 11/1965 | Chisholm | 356/334 |
| 3,447,873 | 6/1969 | Ashley et al. | 356/334 |
| 3,472,595 | 10/1969 | Hashizume | 350/162 |
| 3,563,656 | 2/1971 | Helms | 356/100 |
| 3,578,845 | 5/1971 | Brooks et al. | 356/305 X |
| 3,614,227 | 10/1971 | George | 356/97 |
| 3,765,775 | 10/1973 | Ganssle et al. | 356/195 |
| 3,836,254 | 9/1974 | Barringer | 356/97 |
| 3,861,788 | 1/1975 | Webster | 350/315 |
| 3,877,818 | 4/1975 | Button et al. | 356/186 |
| 3,885,879 | 5/1975 | Louder et al. | 356/100 |
| 4,030,828 | 6/1977 | Suobe et al. | 356/100 |
| 4,030,829 | 6/1977 | Hooper | 356/97 |
| 4,068,954 | 1/1978 | Da Silva | 356/100 |
| 4,070,111 | 1/1978 | Harrick | 356/83 |

OTHER PUBLICATIONS

Strong, *Concepts of Classical Optics,* published by W. H. Freeman and Company, San Francisco, 1958, pp. 577-579 relied on.

*Primary Examiner*—John K. Corbin
*Assistant Examiner*—B. Wm. de los Reyes
*Attorney, Agent, or Firm*—Lane, Aitken, Ziems, Kice & Kananen

[57] ABSTRACT

An improved optical system is disclosed for rapid, accurate spectral analysis of the reflectivity or transmissivity of samples. A concave holographic diffraction grating oscillated at high speed is utilized to provide a rapid scanning of monochromatic light through a spectrum of wavelengths. The grating is positively driven at very high speed by a unique cam drive structure comprising identically shaped conjugate cams. The rapid scan by the grating enables the reduction of noise error by averaging over a large number of cycles. It also reduces the measurement time and thus prevents sample heating by excessive exposure to light energy. A filter wheel having dark segments for drift correction is rotated in the optical path and is synchronous with the grating. Source optics is employed to optimally shape the light source for particular applications. The system optics further includes a unique arrangement of lenses, including cylindrical lenses, to obtain the best light source shape which results in maximum light throughput. Fiber optics are also employed and arranged to meet the optimum requirements of the system for light collection and transmission through portions of the optical system.

24 Claims, 14 Drawing Figures

HOLOGRAPHIC DIFFRACTION GRATING SYSTEM FOR RAPID SCAN SPECTRAL ANALYSIS

BACKGROUND OF THE INVENTION

The present invention relates generally to the field of instruments for spectrally measuring and analyzing optical properties of samples. Such instruments are presently used in industrial and agricultural applications for colorimetry and for quantitatively analyzing the constituents of samples. Additional applications for such instruments are being developed in the field of medicine in which samples are spectrally analyzed for diagnostic purposes.

Examples of agricultural applications presently in use are instruments which accurately determine the oil, protein and water content in grain or soy beans. The traditional analytical laboratory techniques, such as the Kjeldahl technique for measuring protein, are extremely accurate but require the services of a skilled chemist. The results, furthermore, are not immediately or readily available. Buyers of agricultural products have demonstrated an increasing interest in accurate and rapid determinations of the moisture, protein and oil percentages of the various produces purchased. The wheat export market, for example, has seen the widespread introduction of selling on the basis of guaranteed protein content. This competitive pressure has increased the requirement of the commodity handler, from the country elevator to the export terminal, to rapidly and accurately sort grains and other products by their protein percentage, as well as by oil and water content, where applicable. The need for versatile, yet low cost, advanced equipment, which combines and improves upon recent scientific findings in the field of nondestructive testing of agricultural products has greatly increased. For maximum usefulness of commodity handlers, such an instrument must not place high demands on the skillfulness of the operator or require a specialized knowledge of the scientific basis for the end result.

Recent developments have provided instruments which are able to satisfy some of the above requirements of commodity handlers. The optical analyzer described by Donald R. Webster in U.S. Pat. No. 3,861,788, assigned to the assignee of the present application, provides an automatic test instrument for gauging the percentage of various constituents in organic substances by comparing the reflective optical density of the sample at various wavelengths. This device contains narrow band optical filters connected together in the form of a rotatable paddlewheel positioned so that the filters can be individually swept through the incident light path between the specimen and a wideband light source. As the filter wheel turns, the band of light passed by each filter is progressively shifted with the changing angle of the filter relative to the light path. The filter wheel configuration includes opaque vanes extending from the ends of the filters to periodically interrupt the passage of light to the specimen. Photodetectors are positioned to sense the level of light reflected from the specimen. The output of these photodetectors is sampled at predetermined times relative to the rotation of the filter wheel to yield values indicative of reflected intensity at certain wavelengths. An electronic circuit utilizes this data to calculate three optical density difference values corresponding to moisture, protein and oil content of the specimen sample. The difference values are automatically inserted into three linear equations which are solved to obtain readings representing the three percentages of oil, water and protein content of the specimen. Each time a new specimen is loaded for testing, the instrument described in U.S. Pat. No. 3,861,788 is automatically calibrated against a standard sample, preferably Teflon (trademark). The output of the photodetectors is amplified in a special circuit which subtracts the level of dark period current from the output when the photodetectors are illuminated.

A related, but earlier, instrument is described by Eugene R. Ganssle and Donald R. Webster in U.S. Pat. No. 3,765,775, entitled "Optical Internal Quality Analyzer", and also assigned to the assignee of the present application. The specimen sample therein is illuminated with light sequentially filtered by a continuously rotating disc carrying a plurality of narrow bandwidth optical interference filters. The combined output of several photodetectors positioned to receive light transmitted through or, alternatively, reflected by the specimen is selectively sampled after passing through a logarythmic amplifier to obtain readings at two discrete wavelengths which are then compared in a differential amplifier to provide the required measurments. Although the system described in U.S. Pat. No. 3,765,775 is satisfactory for its intended purpose, its ability to make readings at various wavelengths is naturally limited by the number of filters carried by the disc. It is, therefore, not possible to take readings at wavelengths between those of two adjacent filters. This limitation is mitigated somewhat by the filter wheel construction of the aforementioned U.S. Pat. No. 3,861,788.

Yet another recent prior art photo-optical technique for determining, for example, the fat content of meat is described by George F. Button and Karl H. Norris in U.S. Pat. No. 3,877,818 owned by the United States of America. This technique, developed at the U.S.D.A. Agricultural Research Service in Greenbelt, Maryland utilizes an instrument wherein a meat sample is exposed to infrared radiation from an incandescent light source. The radiation is transmitted through or reflected from the meat sample onto a tilting mirror which causes the respective transmitted or reflected light from the meat to pass through a planar interference filter at varying angles of incidence. Varying the angle of incidence of the filter by oscillating the tiling mirror produces a corresponding change in the wavelength of the radiation passing through the filter over a narrow bandwidth in the infrared spectrum. A photodetector receives the light transmitted through the filter and generates an electrical signal that is processed to read the fat content of the sample.

These and other prior art optical analyzers are limited in the accuracy of their measurements by the particular optical components and systems utilized for spectral analysis. The variety of agricultural products requiring very accurate content analysis has increased the demand for optical instruments having greater capability for more precise measurements of constituent content.

SUMMARY OF THE INVENTION

The instrument of the present invention, which is designed for use both in colorimetry and in constituent analysis applications, improves upon the above prior art optical analyzers by providing a novel optical system which achieves greater accuracy at high speed and permits analysis of darker samples than was possible with the prior art high speed systems. In the instrument of the invention, a concave holographic diffraction grating oscillated at high speed is utilized to provide a rapid scanning of the monochromatic light produced at varying wavelengths by the grating. In a concave holographic grating, the lines of the grating are formed by a holographic technique. Concave holographic gratings are presently available on the market and are marketed by J.-Y Diffraction Gratings, Inc. of Metuchen, New Jersey. The use of a concave grating is preferable to plane grating systems because it involves the use of a single optical component as opposed to three or more optical components required in the plane grating systems. As a result, the alignment in calibration procedures are simplifed and the cost of precision mechanical mounts are reduced. The use of a concave holographic grating makes possible the design of a system with low F numbers, for example as low as F/1 in some cases. High performance plane grating systems are usually limited F/4 and higher. The lower optical F numbers makes it possible to pass a greater amount of light energy through the optical system thereby making it possible for the present invention to analyze darker samples than were heretofore possible by prior optical analyzers. In addition, holographic gratings are free of ghosts and have a lower stray light level in comparison to rule gratings. Another advantage of the holographic grating used in the system of the present invention is that it can be made with a very high groove density which enables high resolution while maintaining high light energy throughput. Yet another advantage of the holographic grating is that it is corrected for astigmatic aberration and spherical and coma aberration are also reduced.

The holographic grating in this invention is made to oscillate at very high speed by means of a novel cam drive structure. The cam drive employs two identically shaped conjugate cams to provide positive drive of the grating in both directions. Each cam has a shape selected to make the grating output vary linearly with the angular position of the grating. The cams are also shaped so that different gratings can be used with the same cam drive for different wavelength ranges.

Use of a concave holographic grating permits the grating to disperse light radiation directed at it through an entrance slit into spectral components which are focused along a circle drawn through the entrance slit and the grating. The circle along which these spectral components are in focus is known as a Rowland circle. The exit slit is positioned such that each respective spectral component dispersed by the grating is optimized for best focus and minimum aberrations at the exit slit as the grating is oscillated to scan the wavelength range.

Because the holographic grating is oscillated at very high speed, a rapid scan technique is possible enabling the present invention to eliminate noise by averaging over a large number of cycles. More specifically, in the system of the present invention, the grating is oscillated at about 300 cycles per minute which, at two scans per cycle, provides 10 scans per second. At the end of each scan, a dark period is provided in order to permit drift correction. The dark period is provided by a filter wheel which has two dark segments arranged 180 degrees apart. The wheel is synchronized with the cam drive of the grating so that each respective dark segment corresponds to the grating orientation at one of its extreme positions in the oscillation cycle. The output can be measured by a photodetector during the dark periods to provide the necessary drift correction.

Another feature of the present invention involves the use of a polarizer at the entrance slit to polarize the light passing through the entrance slit irradiating the grating. The polarizer can be rotated to 90 degrees so that the axis of polarization can be varied.

The present invention further provides a novel technique for modifying the shape and size of the light source to meet the optimum requirements of the system. Present optical devices requiring white light sources for producing wide band radiation generally utilize an incandescent bulb typically including a tungsten filament. The shape and size of the filaments contained in commercially available bulbs are limited and are usually inadequate to satisfy the optimum demands of the optical systems. By providing a reflector positioned with respect to the light source to form a real image of the filament on top of or below the actual filament, the length of the filament can be effectively doubled so that an image of the "lengthened" filament source will completely fill the entrance slit with light. In another embodiment of the present invention, the reflector is positioned so that the filament is imaged next to itself to produce a source of light shaped as a square to approximate a circular light source.

The aforementioned optical modification to lengthen the filament permits optimization of the aspect ratio of the slit optics in the present invention. Since the ratio of the height of the entrace slit to its width in typically about 5.5, the abovedescribed optical modification permits the ratio of the filament height-to-width to approach the same 5.5 relationship and thereby completely fill the slit with source light. The alternative optical modification, producing an approximate circular light source, provides the ideal light source shape for projection of white light on the sample.

Both of the techniques for modifying the shape of the light source are achieved by a single manufactured structure in which the reflector it tiltable on a vertical axis passing through the reflector and is rotatable about an axis colinear with the optic axis of the source optics. By correctly adjusting the tilt of the reflector about the vertical axis and the rotational position of the reflector about the optic axis, the image of the filament can be positioned either to double the effective length of the filament or to widen it into a square.

Yet another improvement in the present invention involves an unique arrangement in one embodiment of optical lenses utilizing a cylindrical lens at the entrance slit for imaging the height of a spherical lens through which the light passes on the grating. This arrangement assures that the vertical dimension of the source illumination on the grating corresponds to the height of the grating. A second cylindrical lens is provided at the exit slit for virtually imaging the width of the exit slit back on the grating. Since the width of the exit slit imaged back on the grating and the height of the grating now remain constant regardless of the oscillation of the grating, the grating will project a monochromatic light image on the sample which is fixed in shape and size regardless of the oscillation of the grating.

The projection of the constant size monochromatic light image is further accomplished in the above described embodiment by means of additional lenses and by providing a variable aperture iris at a point where a real image of said monochromatic light image is projected. By changing the size of the iris aperture, the amount and size of the illumination projected on the sample can then be controlled.

Photodetectors are provided in the above described embodiment of the present invention to detect light radiation being either transmitted through or reflected by the sample according to the preferred application. Alternatively, the present invention provides for modification of the output detection by including fiber optics for effectively collecting light transmitted or reflected by the sample. The output of the fiber optics is then focused onto a photodetector for sample spectral analysis.

A further improvement of the present invention is an alternative optical arrangement utilizing the approximate circular light source described earlier to project white rather than monochromatic light on the sample. In this embodiment, the sample is located at the input of the optical system and light reflected by or, alternatively, transmitted through the sample is collected by a plurality of optical fibers arranged, for example, in a circular array. The other end of this fiber optics array is arranged linearly whereby the ends of the fibers form an entrance slit. Light is effectively transmitted through the fibers by internal reflection to completely fill the entrance slit so formed. The optical parameters of this fiber optics array are chosen such that each of the fibers accepts a cone of light reflected by or transmitted through the sample which is equal in angle to the acceptance cone of the grating. The light exiting from the linearly arranged end of the fibers will, therefore, project the light on the oscillating grating at an angle which will permit the light to completely fill the vertical dimension of the grating with all the light accepted and transmitted by fiber optics array. This improved design permits optimum utilization by the grating monochrometer of the light intensity transmitted through or reflected by the sample. The grating in this embodiment is also oscillated at very high speed as described earlier and provides spectral dispersion of the light at an exit slit. The spectral light passing through the exit slit is then sensed by a photodetector for spectral analysis of the sample.

Further objects and advantages of the present invention will become apparent by reference to the following detailed description of the preferred embodiments considered in conjunction with the accompanying drawings.

BRIEF DESCRIPTION OF THE DRAWINGS

FIG. 11 is a schematic drawing of a plan view of a portion of FIG. 8 illustrating the light source optics and the fibers optics utilized in this second preferred embodiment;

DETAILED DESCRIPTION OF THE PREFERRED EMBODIMENTS

Figures 1, 2, 3:
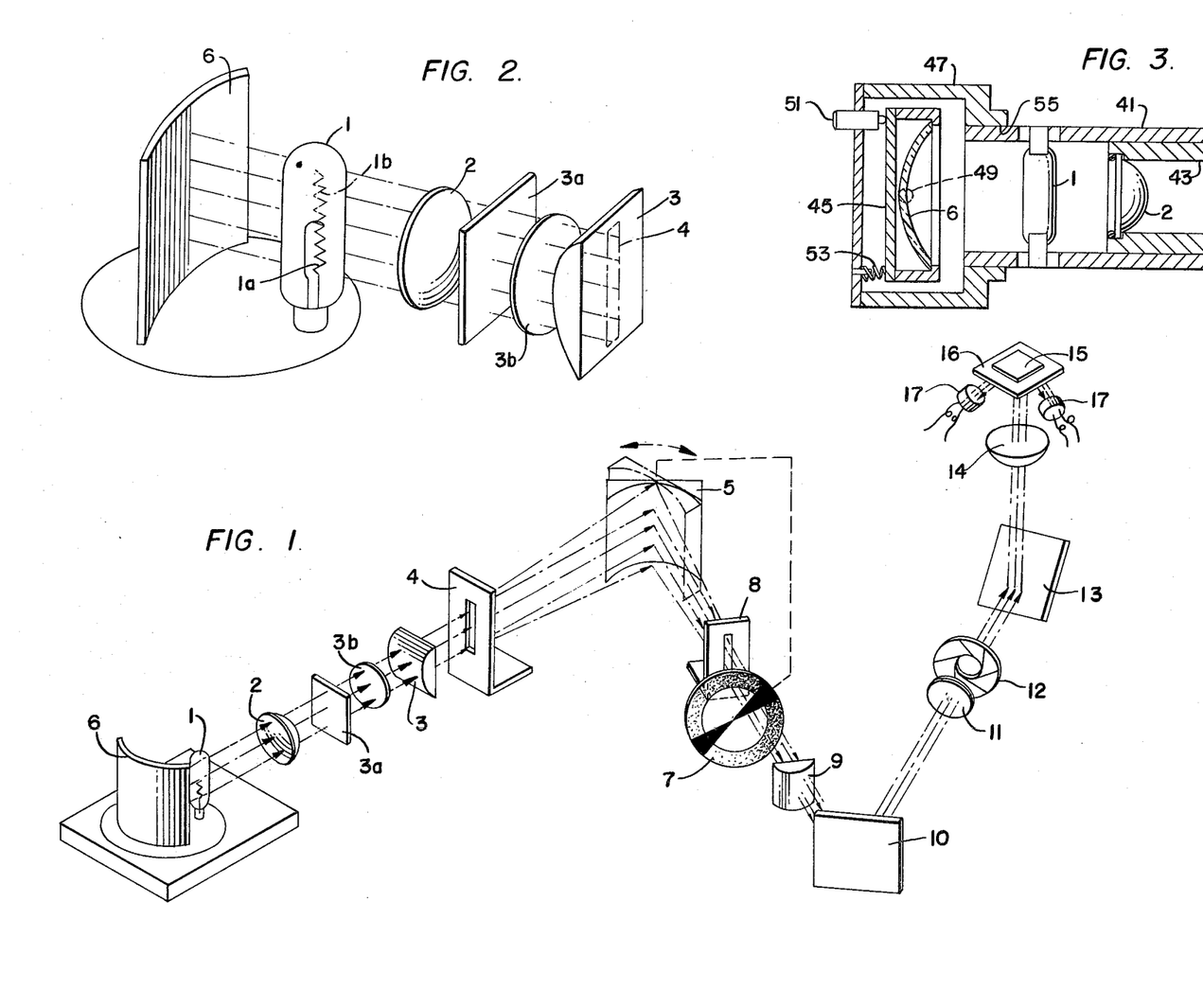
FIG. 1 is a schematic perspective view of a preferred embodiment of the present invention utilizing an oscillating holographic grating wherein monochromatic radiation reflected by the sample is detected for spectral analysis.
FIG. 2 is a schematic diagram illustrating the light source optics of FIG. 1.
FIG. 3 is a sectional view illustrating the mounting system for a portion of light source optics of the system.
Figure 2:
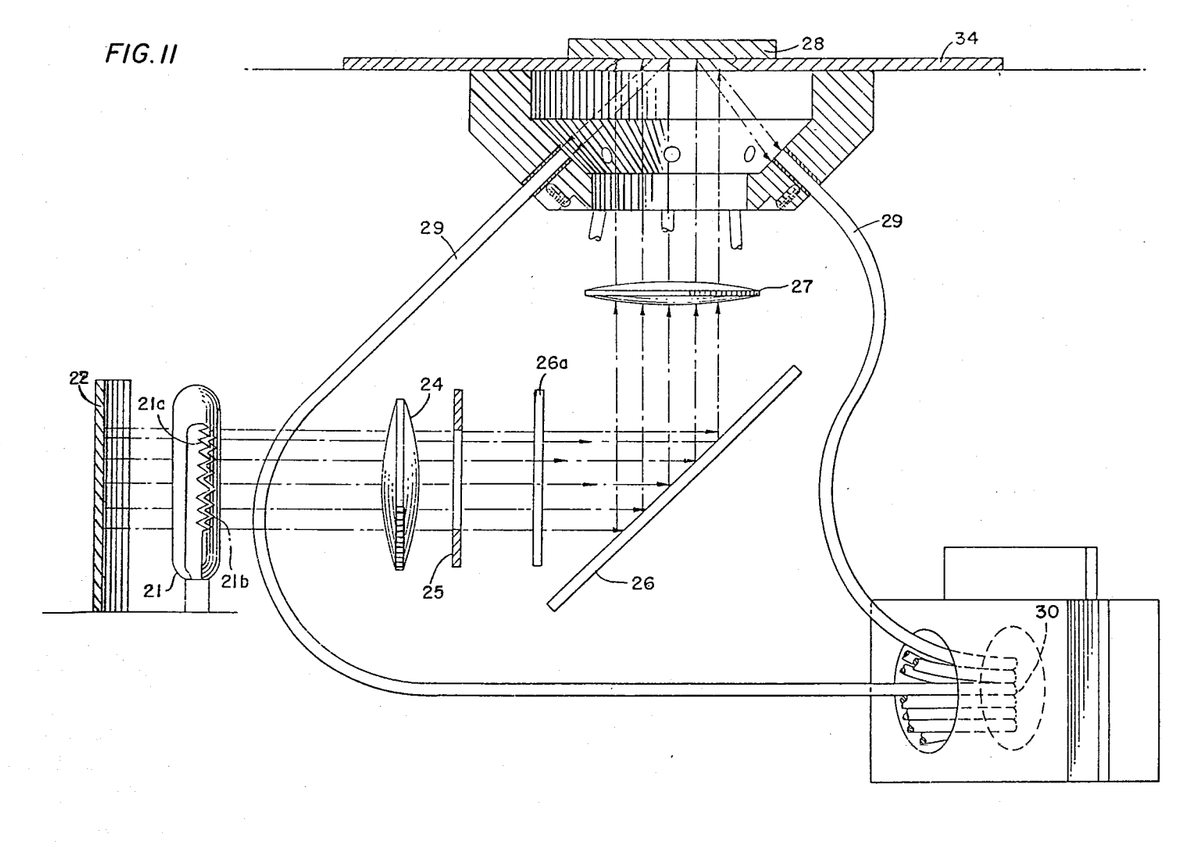

In the schematic illustration of FIG. 1, the spacings of some of the components of the system has been exaggerated to facilitate illustration. As shown in FIG. 1, a tungsten filament light bulb source 1 emits wide band white light. The light from the tungsten filament is collected by a spherical lens 2 and is imaged on an entrance slit 4. A cylindrical lens 3 assures proper filling illumination of the concave holographic diffraction grating of the system designated by reference number 5. The lens 3, while shown spaced from the slit 4, will actually be positioned immediately adjacent to the slit 4.

A polarizer 3b for linearly polarizing the light may be provided in the light path between the filter 3a and the cylindrical lens 3. The polarizer may be rotated about the optical axis through 90 degrees so that the axis of polarization can be varied. The polarizer, which serves to make possible irradiation of the sample with polarized light, is useful in constituent analysis applications in which the axis of polarization will be selected experimentally to give the most accurate determinations of the constituents of the sample.

The novel source optics is more clearly illustrated in FIG. 2, wherein the reflector 6 is positioned with respect to the filament 1a of the tungsten filament light source 1 so that an image 1b of the filament 1a is formed immediately above the filament 1a, thereby effectively doubling the length of the tungsten filament. This optical modification is important in the present optical system since commercially available tungsten filament lamps do not have filaments with a height-to-width ratio corresponding to the height-to-width ratio of the entrance slits, such as slit 4, commonly used in monochrometer optical systems. By effectively doubling the length of the filament 1a by means of reflector 6, a linear filament light source is provided which will approximately correspond to the aspect ratio of the entrance slit 4. The spherical lens 2 forms an image of the filament and the adjacent filament image on the entrance slit 4 to completely fill the entrance slit 4 with illumination. The axis of curvature of the cylindrical lens 3 is horizontal and this lens serves to focus the vertical dimension of the spherical lens 2 on the grating 5 so as to make the vertical dimension of the illumination on the grating correspond to the height of the grating. An infrared filter 3a filtering out infrared light is provided to reduce stray source light and unnecessary heat energy produced by the source. Altneratively, a filter may be utilized in place of infrared filter 3a to pass infrared radiation when the grating and other components of the optical system are chosen for infrared analysis of the sample.

The sectional view in FIG. 3 illustrates the mechanism for mounting the reflector 6 in order to adjust it to the position to form the image of the filament in the desired position. As shown in FIG. 3, the light source 1 is mounted in a tube 41 in which the lens 2 is also mounted with its optic axis in alignment with the center line of the tube 41. The lens 2 is actually mounted in a sleeve 43 which is axially slidable in the tube 41 to permit adjustment of the axial position of the lens 2 for the purposes of properly adjusting the focus of the lens 2. The reflector 6 is mounted in a support member 45 which, in turn, is pivotally mounted in a round, hollow support member 47, the support member 45 being pivotal with respect to the support member 47 on an axle 49 positioned so that the pivot axis is perpendicular with the optical axis of the lens 2 and is in alignment with the reflector surface at the middle thereof. A set screw 51 is threaded through the back wall of the support member 47 to engage the back of the support member 45 positioned spaced from the axle 49. A compression spring 53 is positioned between the back of the support member 45 and the back wall of the support member 47 and engages the back wall of the member 45 spaced from the axle 49 on the opposite side from the set screw 51. As the set screw 51 is advanced, it will pivot the support member 45 and, therefore, the reflector 6 on the axle 49 against the force of the spring 53. Thus, by adjusting the set screw 51, the angular position of the reflector 6 with respect to the support member 47 can be adjusted. The support member 47 defines a cylindrical surface 55 which engages the outer cylindrical surface of the tube 41 so as to make the support member 47 rotatable with respect to the tube 41 about the optical axis of the lens 2.

In order to employ the mechanism shown in FIG. 3 to position the image of the filament in alignment with the filament itself as illustrated in FIG. 2, the angular position of the reflector 6 with respect to the support member 47 is adjusted by means of the set screw. This adjustment positions the image 1b of the filament 1a at a selected distance from the filament 1a, the distance changing as the reflector is pivoted on the axle 49. When the reflector 6 has been pivoted to space the image 1b from the filament 1a, rotation of the support member 47 about the tube 41 will rotate the image 1b about the image 1a. Thus, by combined adjustment of the angular position of the reflector 6 with respect to the support member 47 and the angular position of the support member 47 with respect to the tube 41 and the source 1, the filament image 1b can be brought into the position illustrated in FIG. 2 where it is aligned with the filament 1a and spaced therefrom by an amount to be a continuation of the filament 1a. The same mechanism shown in FIG. 3 is used in another embodiment of the invention in which the image of the filament is positioned to make the light source in the form of a square as is described in more detail below.

Grating 5 is a concave holographic grating of the type discussed earlier which is made to oscillate at very high speed in both directions, as generally indicated by the arrow in FIG. 1, by a cam drive structure which will be further discussed below with reference to FIG. 11. The oscillation of the grating 5 is synchronized with the rotation of filter wheel 7 about its axis, the synchronization being schematically represented in FIG. 1 by the dashed line from grating 5 to filter wheel 7.

Holographic grating 5 disperses the white illumination imaged on it through the entrance slit 4 into spectral components which are focused at the exit slit. Alternatively, a holographic grating may be used which disperses infrared radiation when infrared analysis of the sample is contemplated.

Cylindrical lens 9, the axis of curvature of which is vertical as distinguished from cylindrical lens 3 wherein the curvature axis is horizontal, virtually images the width of exit slit 8 back on the grating 5. Because the width of exit slit 8 imaged on the grating 5 and the height of the grating are constant regardless of the oscillation of the grating, constant size illumination of a sample with the light dispersed by the grating can be efficiently achieved even though the grating is oscillating. The oscillation of grating 5 will vary the wavelength but not the size or shape of the illumination on the sample.

The projection of the constant size monochromatic illumination is accomplished by means of the additional lenses and mirrors illustrated in FIG. 1 comprising the unique output optics of this preferred embodiment. Since cylindrical lens 9 has provided an image of the width of exit slit 8 on the grating 5, an image object is formed at the grating comprising a composit of the grating height and the virtual lamp of the exit slit width. After the beam of light passes through filter wheel 7, it is reflected by mirror 10 to a spherical lens 11. Spherical lens 11 forms a real image of the composit of the slit width and grating height at a variable aperture iris 12. Because the width of the slit is constant and the height of the grating is constant, this real image formed at the iris aperture 12 will be of constant size. If the cylindrical lens 9 were not present, the image formed at the iris aperture 12 would vary in width as the grating changes its angular position. By changing the size of the opening (F-stop) of the iris aperture 12, the amount and size of illumination from the real image so produced at iris 12 for illuminating the sample 15 can be controlled. The illumination from the image formed at iris 12 is then reflected by mirror 13 to spherical lens 14, which takes the image that was formed at the iris 12 and focuses it on the sample 15 which has been positioned on supporting plate 16. Because the image at the iris 12 is of constant size, the image on the sample will be of constant size. The light diffusively reflected from sample 15 is then sensed by photodetectors 17 for spectral analysis.

Figure 4:
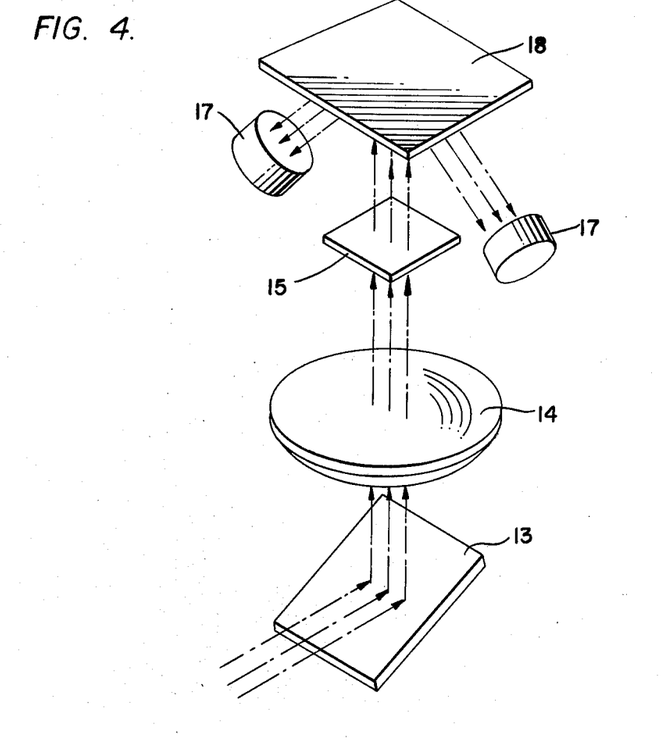
FIG. 4 is a diagrammatic illustration of a modification of FIG. 1 wherein monochromatic radiation transmitted through the sample is detected for spectral analysis.

FIG. 4 illustrates a modification of the preferred embodiment in FIG. 1 wherein sample 15 is positioned to permit the monochromatic illumination to be transmitted through the sample. The illumination from the iris 12 is reflected by mirror 13 and focused by spherical lens 14 through sample 15 on a diffusive white reflector 18. The radiation transmitted by sample 15 is reflected by the white reflector 18 and sensed by photodetectors 17 for subsequent spectral analysis of the sample. Alternatively, the sample 15 may be positioned adjacent to the variable aperture iris 12 in FIG. 1 so that illumination passing through iris aperture 12 and transmitted through the sample 15 will be subsequently sensed by photodetectors 17.

Figure 7:
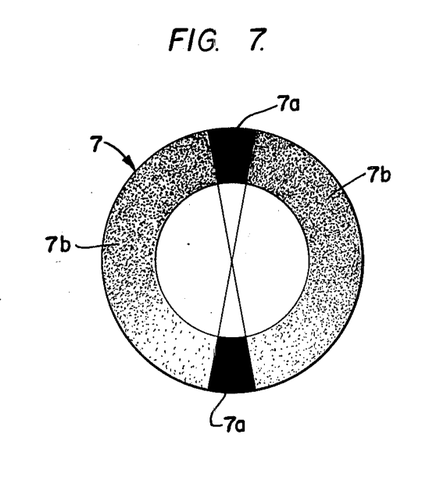
FIG. 7 is an illustration of the segmented filter wheel utilized in the system.

The filter wheel 7 shown in FIG. 1 is driven by a motor so as to be synchronized with the oscillation of grating 5. Referring to FIG. 7, a plan view of filter wheel 7 is there illustrated. The filter wheel 7 has two dark segments 7a arranged 180 degrees apart and two circular segments 7b running between the two dark segments. Each circular segment is a narrow bandwidth filter having linearly changing wavelengh transmission bands such that the portion of each segment closer to the top of the filter wheel 7 will pass higher wavelengths than that portion closer to the bottom of the filter wheel. Filter wheel 7 is so constructed that one side of the filter is a mirror image of the other side about a line passing through the middle of the opaque or dark segments 7a.

For each complete oscillation of the grating 5, the filter wheel 7 will revolve 360 degrees about its axis and is arranged to position each respective dark segment 7a to interrupt or block the light passing through the exit slit 8 at each corresponding extreme position of the grating in its oscillation cycle. The output of the optical system can be measured by photodetectors 17 during these dark periods to provide the necessary drift correction. The filter wheel 7, in addition to limiting stray light, also eliminates second order light which will be half the wavelength of the primary light. For example, if light is being transmitted through the exit slit at 800 nanometers in wavelength, there will also be some light transmitted at 400 nanometers. The filter wheel 7 serves to eliminate this light as well.

Figures 5, 6:
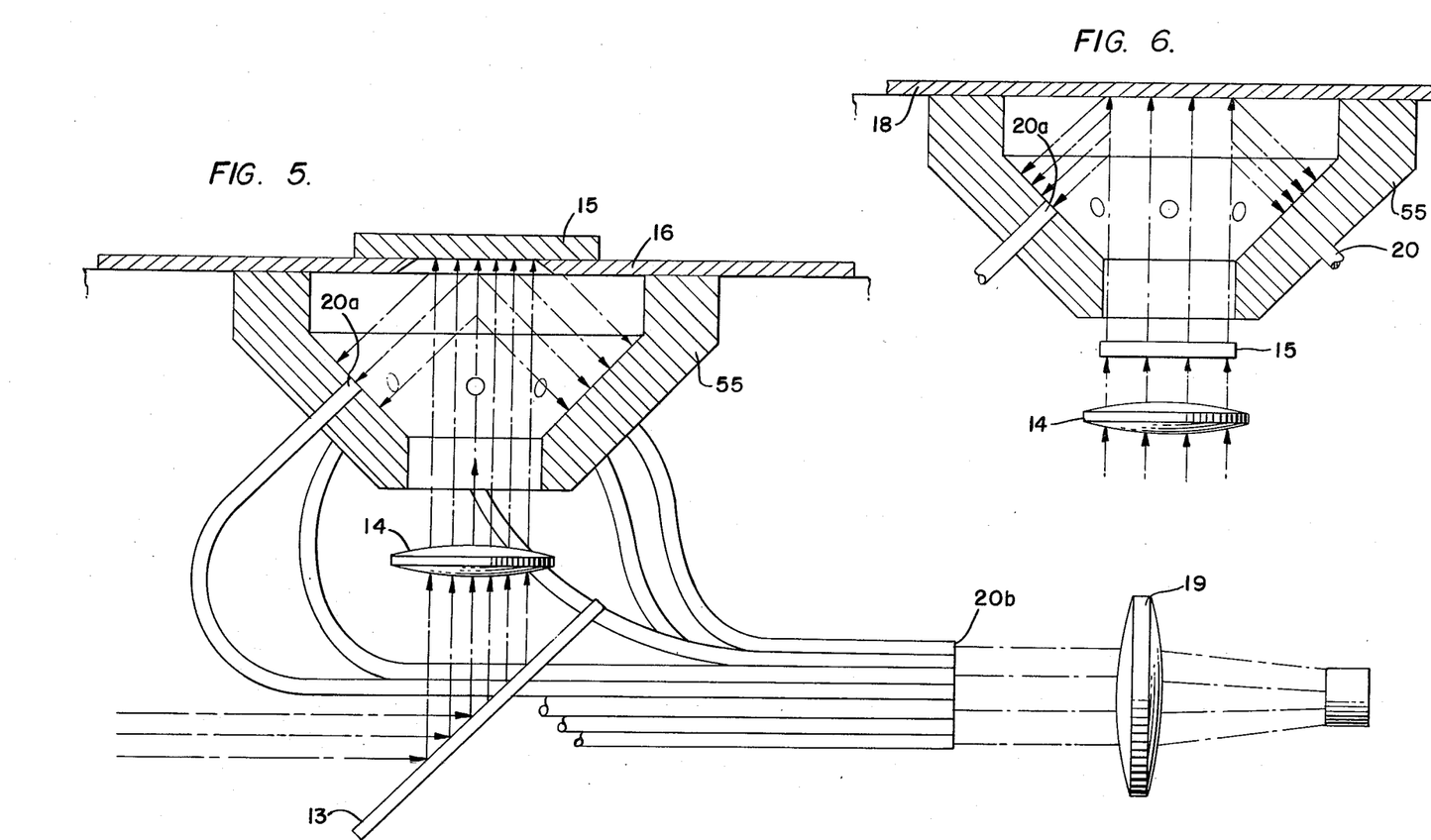
FIG. 5 is a schematic diagram illustrating yet another modification of FIG. 1 wherein monochromatic radiation reflected by the sample is collected by fiber optics and transmitted to a photodetector.
FIG. 6 is a scehmatic diagram illustrating a similar modification as in FIG. 5 for collecting the radiation transmitted through the sample.

FIGS. 5 and 6 illustrate yet further modifications of the optics associated with the sample in FIGS. 1 and 4, respectively. In FIG. 5, for example, instead of positioning the photodetectors 17 to directly receive light reflected by sample 15 as in FIG. 1, fiber optic bundles 20 are disposed to collect and transmit this reflected light to the photodetector 17 by means of internal reflection. The fiber optic bundles are arranged so that the endfaces 20a of each fiber bundle are positioned to form circular distribution facing the sample on a conical locus so as to collect the illumination being reflected by sample 15. The endfaces 20a are mounted on a conical support member 55, which may be made transparent to reduce the amount of stray light reflected by the support member. As in FIG. 1, mirror 13 reflects the illumination of the image formed at iris 12 which is then focused by lens 14 on sample 15. The illumination reflected by the sample is collected by the fiber bundles at their endfaces 20a and transmitted to the opposite endfaces 20b of the fiber bundles. Endfaces 20b are arranged in a plane to form a circle. The light emitted from endfaces 20b is then focused by lens 19 on photodetector 17 for spectral analysis. The photodetector will be substantially smaller than the circle formed by the endfaces 20b of the fiber bundles. The lens 19 focuses all of the light emitted from the end surfaces 20b into a spot on the photodetector corresponding in size to the size of the photodetector.

In FIG. 6, a similar modification is shown with respect to the photodetection of radiation transmitted through the sample 15 previously illustrated in FIG. 4. Monochromatic light is focused by lens 14 through the sample 15 onto white diffusive reflector 18. The light reflected by reflector 18 enters endfaces 20a of the fiber optic bundles 20, again arranged in a conical circular distribution in support member 55, and is transmitted by the bundles 20 to the opposite endfaces for projection on and detection by a photodetector as explained in connection with FIG. 5. Alternatively, the sample 15 may be positioned adjacent variable aperture iris 12 in FIG. 1 so that illumination passing through iris aperture 12 and transmitted through the sample 15 will be subsequently sensed by photodetector 17 after being collected by and transmitted through fiber optics 20.

Figure 8:
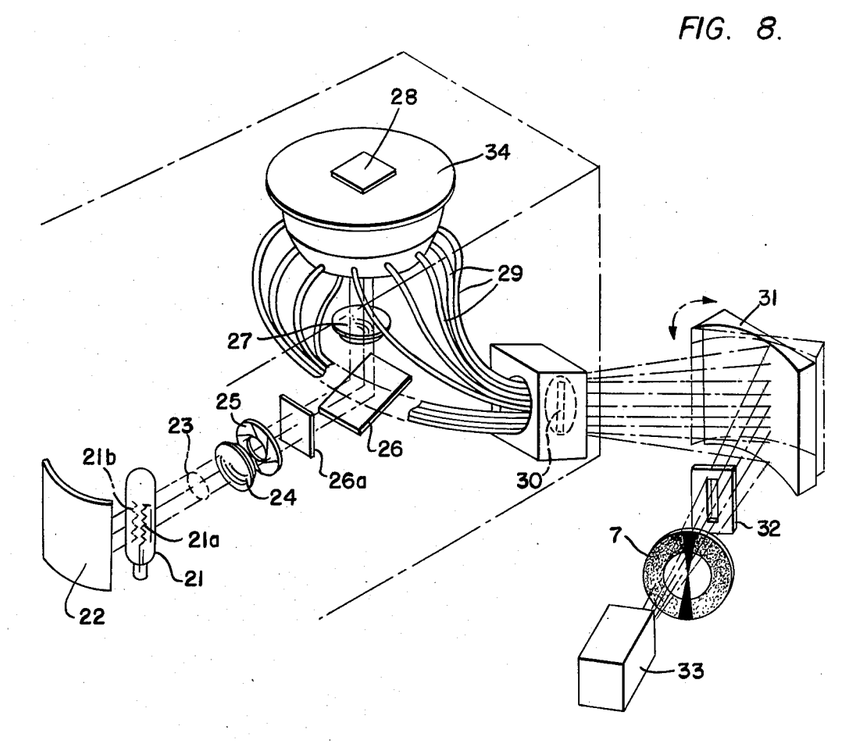
FIG. 8 is a perspective view of a second preferred embodiment of the present invention utilizing an oscillating holographic grating wherein white illumination reflected from a sample is collected by fiber optics and transmitted to the grating for dispersion and detection for spectral analysis.
Figure 9:
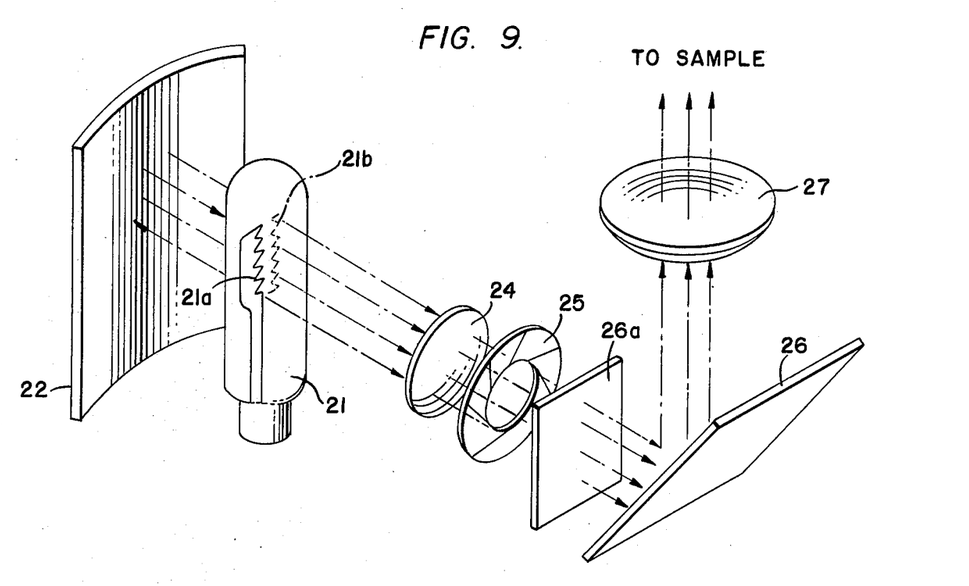
FIG. 9 is a schematic diagram illustrating the light source input optics of FIG. 8.

A perspective view of a second preferred embodiment of the present invention is shown in FIG. 8. Wide band white light illumination from a tungsten filament light bulb source 21 is projected by the optics shown to form a spot of illumination on sample 28. The novel source optics is more clearly illustrated in FIG. 9 wherein the tungsten filament light source 21 is shown having a filament 21a. Since in this embodiment, the sample is to be illuminated by white light rather than the monochromatic illumination utilized in FIG. 1, the ideal shape of the illumination to be projected on the sample should be a spot or circle of light. Since tungsten filaments are not commonly formed in circular shapes, the present embodiment contemplates optically modifying the tungsten filament light source in order to achieve this goal. To this end, a reflector 22 is positioned as shown in FIG. 8 to form an image 21b of filament 21a along side of itself. The light source so formed is shaped as a square, which more clearly approximates the ideal shape of a circle than the linear filament. The square filament source is imaged by lens 24 on lens 27. The latter lens 27 in turn will project an image of the illumination at iris 25 on the sample. The variable aperture iris 25 is positioned adjacent to lens 24 to control the size of, and, therefore, the amount of illumination being projected on the sample. Mirror 26 is necessary to "fold" the light illumination from the source upwards toward the sample. An infrared filter 26a is provided to reduce stray source light and unnecessary heat energy produced by the source. Alternatively, a filter may be utilized in place of infrared filter 26a to pass infrared radiation when the grating and other components of the optical system are chosen for infrared analysis of the sample.

An advantage of using the two lenses 24 and 27 as described above is that this arrangement produces a nearly round spot of light on the sample, which is variable in size. Because the shape of the light source by the operation of the reflector 22 producing an image of the filament next to itself has made it approximately square in shape, the illumination passing through the lens 24 will substantially fill the lens 24. As a result, when the lens 27 focuses an image of the iris which is adjacent to lens 24 on the sample 28, it produces an almost uniform round circle of light on the sample.

To achieve the positioning of the image 21b so that the filament 21a and the image 21b form the shape of a square, the same mechanism illustrated in FIG. 3 is used. Thus, a single manufactured part serves both in the embodiment in which the sample is irradiated with wide band light used in the embodiments in which the sample is irradiated with narrow band light after it has been dispersed by the grating.

The entire input optics is schematically shown in FIG. 11, which is a sectional view in elevation of a portion of FIG. 7. The circle or spot of light projected on sample 28, which as been positioned on a supporting plate 34, by means of the optics described above, is diffusively reflected by sample 28. The reflected illumination is collected by the endfaces of a fiber optics array 29 which is comprised of a plurality of individual fiber bundles arranged at one end on a conical locus to receive reflected illumination from the sample. The ends of the fiber bundles are mounted in a conical member 57 which may be made transparent to reduce the amount of stray light reflected by the support member. At the other end, the ends of the fiber bundles of the fiber optics array 29 are arranged linearly to form an entrance slit 30. Light reflected by sample 28 is therefore effectively transmitted through the fibers by internal reflection to completely fill the entrance slit 30. The optical parameters of the fiber optic array 29 are chosen such that each fiber accepts a cone of light reflected by the sample 28 which is equal in angle to the acceptance cone of the grating 31.

Referring again to FIG. 8, the light exiting from the linear endface 30 formed by the fiber optics array 29 will, therefore, project the light transmitted by the array 29 on the grating 31 at an angle which will permit the light to completely fill the grating 31 with all the light illumination accepted and transmitted by the fiber optics array 29. This improved design utilizing the fiber optics array 29 permits optimum utilization by the grating 31 of the light intensity reflected by the sample 28 and transmitted through the fiber optics 29.

The grating 31 in this embodiment is also oscillated at very high speed as described earlier in connection with the embodiment of FIG. 1 and provides rapid scanning of the spectral light dispersed at an exit slit 32. The monochromatic light passing through exit slit 32 is sensed by photodetector 33 for spectral analysis of the sample. Alternatively, a holographic grating may be used which disperses infrared radiation when infrared analysis of the sample is contemplated.

A filter wheel 7 of the identical structure as filter wheel 7 of FIG. 7 is positioned immediately after the exit slit 32 in FIG. 8. Filter wheel 7 is synchronized with the oscillation of grating 31 for the identical purpose as was filter wheel 7 in FIG. 1.

Figure 10:
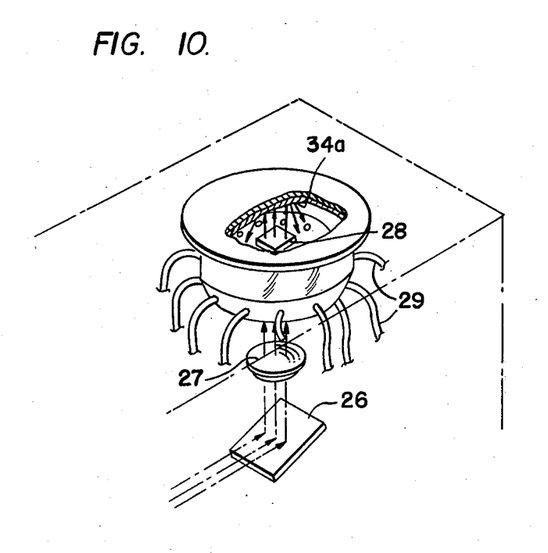
FIG. 10 is a diagrammatic illustration of a modification of FIG. 8 wherein the fiber optics collects the illumination which is transmitted through the sample.

The embodiment of FIG. 8 can be further modified to detect radiation transmitted by the sample as shown in FIG. 10. The sample 28 is so arranged that the spot of source light transmitted through sample 28 is reflected by a diffusive white reflector 34a. The reflected light is then collected by the endface of the fiber optic array 29, as described in connection with FIG. 8, and is transmitted through individual fibers of array 29 by internal reflection to their opposite ends forming entrance slit 30. The operation is then exactly the same as described in connection with FIG. 8 above.

Figure 12:
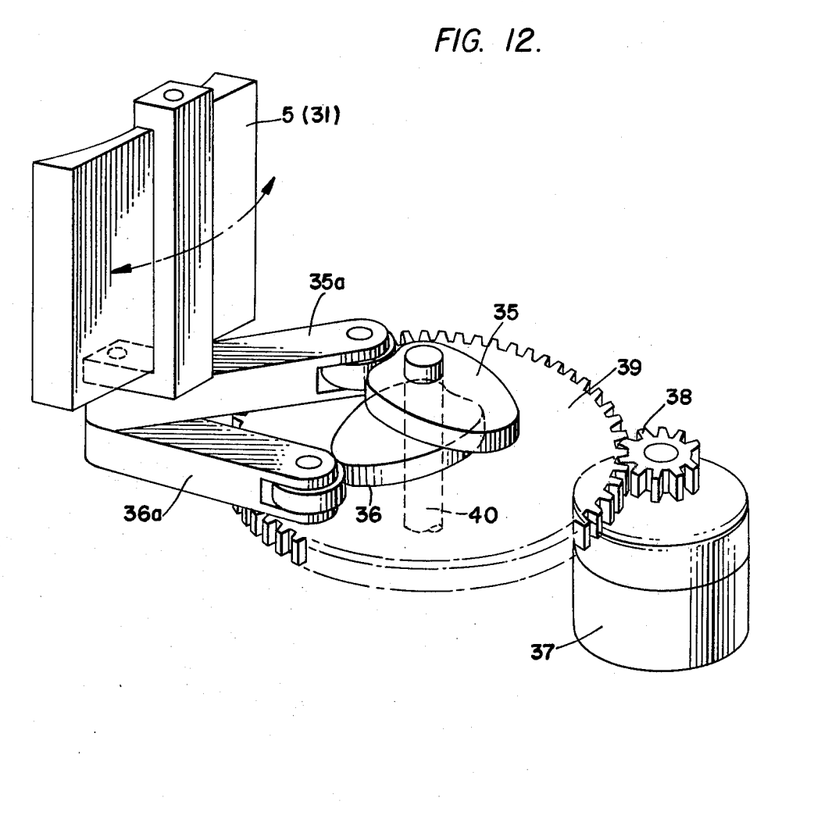
FIG. 12 is a perspective view illustrating the cam drive structure utilized in the present invention to oscillate the holographic grating at very high speed.

FIG. 12 schematically illustrates the cam drive structure for oscillating grating 5 of FIG. 1 or grating 31 of FIG. 7 at very high speed. The cam drive employs two identically heart-shaped conjugate cams 35 and 36 to provide positive drive of the grating in both directions as shown by the arrow. The shape of the cams has been selected to make the grating output vary linearly with the angular position of the grating and to, furthermore, permit different gratings to be used with the same cam drive for different applications. Each conjugate cam has a cam follower associated therewith depicted in FIG. 12 as 35a and 36a. The conjugate cams 35 and 36 are driven by a high speed motor 37 through gears 38 and 39. Cam followers 35a and 36a track the lateral surfaces of their respective heart-shaped cams 35 and 36 as the latter are rotated about their axis by pin 40 which is driven by motor 37 through gears 38 and 39. As the cam followers track the conjugate cams, they cause the grating to oscillate at very high speed.

Figure 13:
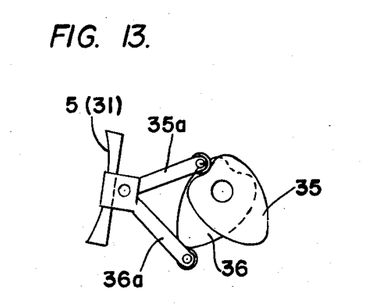
FIGS. 13 and 14 are schematic representations of two different positions of the cams and cam followers during the oscillation cycle of the grating.
Figure 14:
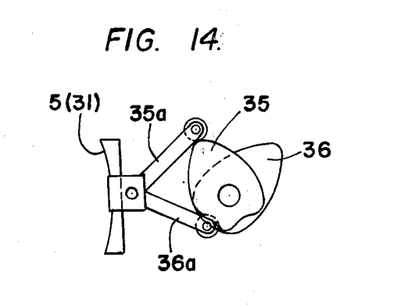

FIGS. 13 and 14 are schematic representations of the two extreme positions of the grating in its oscillation cycle and the respective positions of the conjugate cams and their cam followers. In FIG. 13, for example, the grating is shown at one extreme position in its oscillation cycle corresponding to cam follower 36a being at the maximum throw of cam 36 while cam follower 35a is at the minimum throw of cam 35. In FIG. 14, the opposite extreme position of the grating is shown wherein the opposite relationship exists with respect to the cams and their followers. In FIG. 14, cam follower 35a is now on the maximum throw of cam 35 while cam follower 36a is on the minimum throw of cam 36.

With the above described cam system, each acceleration and deceleration of the grating during its oscillation is effected by the action of one of the cam surfaces pushing on a cam follower and no spring is required to maintain either of the cam followers in engagement with the corresponding cam surface. As a result, the cam drive enables the holographic grating to be oscillated at a very high speed, for example 300 cycles per minute, to thereby permit the grating to rapidly scan the exit slit ten times per second. This rapid scanning makes it possible for the present invention to eliminate noise by averaging over a large number of oscillation cycles.

The rotation of the filter wheel 7 in the embodiments of FIGS. 1 and 8 is, of course, synchronized with the cam drive of FIG. 12 as described earlier so that each revolution of the filter wheel 7 will correspond to one complete oscillation cycle of the grating. Further as described above, filter wheel 7 is initially oriented so that one dark segment 7a of the filter wheel will block the light path when the grating and the cam drive are in the position shown by FIG. 13. The opposite dark segment 7a of filter wheel 7 will likewise block the light path when the grating and the cam drive are in the position shown by FIG. 14. The exact manner in which the filter wheel rotation is synchronized with the grating oscillation is not shown in the drawings but can be easily implemented by those skilled in the art by means of, for example, additional gears associated with motor 37 and gears 38 and 39 of FIG. 12 for driving the filter wheel.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. Optical apparatus for analyzing a sample comprising a concave diffraction grating operable to disperse impinging light radiation into narrow bandwidth components, means to oscillate said diffraction grating, optical means for projecting light radiation on the oscillating grating, an entrance slit located between said optical means and the grating, an exit slit positioned to receive the light radiation dispersed by said grating, photosensing means for detecting light radiation that has passed through said exit slit, a wheel located in the path of said dispersed light radiation having at least one dark segment and at least one light transmitting segment, and means to rotate said wheel in synchronism with the oscillation of said grating so that said dark segment is positioned to interrupt the light radiation when said grating is at one of its extreme positions.

2. The optical apparatus of claim 1, wherein said means to oscillate said grating comprises conjugate cams for providing a positive drive by the cam surfaces to said grating in both directions of the oscillation.

3. The optical apparatus of claim 2, wherein said conjugate cams are shaped to provide a grating output varying linearly with the angular position of said grating.

4. The optical apparatus of claim 1, wherein there is provided means to position a sample material in the path of radiation that has passed through said exit slit and wherein said optical sensing means detects radiation from said sample material.

5. The optical apparatus of claim 4, wherein optical sensing means detects radiation reflected by the sample material.

6. The optical apparatus of claim 4, wherein said optical sensing means detects radiation transmitted through the sample material.

7. The optical apparatus of claim 1, wherein said wheel is divided into four segments including two dark segments on opposite sides of said wheel with light transmitting segments extending on opposite sides of said wheel between said dark segments, said light transmitting segments comprising band pass filters with transmission bands linearly changing with the angular position on said wheel, the light transmitting properties of the light transmitting segments being arranged to be mirror images of one another about an axis passing through the middle of said dark segments, said means to rotate said wheel in synchronism with the oscillation of said grating positioning said dark segments to interrupt the light radiation when said grating is at both of its extreme positions in its oscillation cycle.

8. The optical apparaus of claim 1, wherein there is provided means to position the sample to be analyzed, and means to irradiate said sample with light radiation, said optical means comprising means to project radiation from said sample on said grating.

9. The optical apparatus of claim 8, wherein said optical means projects radiation reflected by said sample onto said grating.

10. The optical apparatus of claim 8, wherein said optical means projects radiation transmitted through said sample of said grating.

11. Optical apparatus for analyzing a sample comprising a filament lamp having a filament, reflector means for producing a real image of said filament in adjacent axial alignment therewith to form a composite image object of a filament of increased length, a diffraction grating operable to disperse impinging radiation into narrow bandwidth components, an entrance slit for said grating positioned to pass the light passing through said entrance slit to be projected onto said grating, and means to focus an image of the composite image object of said filament on said entrance slit to fill said entrance slit with light.

12. Optical apparatus as recited in claim 11, further comprising means to oscillate said grating, an exit slit positioned to receive the radiation dispersed by said grating as said grating oscillates, means to position a sample in the path of radiation passing through said exit slit, a photosensing means to detect radiation from said sample material.

13. Optical apparatus for analyzing sample comprising a grating, means to project light radiation on said grating, means to oscillate said grating, an exit slit positioned to receive the light dispersed by said grating as said grating oscillates, a cylindrical lens positioned in the path of the light passing through said exit slit to produce a virtual image of the width of said exit slit on said grating, means for positioning a sample to be analyzed, optical means to focus from the radiation passing through said cylindrical lens a real image of the composite of the virtual image of the width of said slit at said grating and the heighth of said grating and to project the radiation on said sample, and photosensing means for detecting radiation from said sample.

14. Optical apparatus for analyzing a sample material comprising a concave diffraction grating operable to disperse impinging radiation into narrow bandwidth components, means to oscillate said diffraction grating, optical means for projecting light radiation on said grating, an entrance slit located between said first optical means and said grating, an exit slit positioned to receive the radiation dispersed by said grating as it oscillates, means to position a sample in the path of radiation passing through said exit slit, a fiber optic array comprising a plurality of fibers, one end of each of said fibers having their end faces arranged in a conical locus positioned for said fibers to receive radiation from said sample, the other end of said fibers having their end faces arranged in a planar circular shape and photosensing means positioned to receive the light radiation emitted from the other end of said fibers.

15. The optical apparatus as recited in claim 14, wherein said sample has a planar surface positioned in the path of said radiation and the said conical locus is positioned so that the ends of said fibers receive light reflected from said surface with the axis of said conical locus perpendicular to said surface.

16. Optical apparatus as recited in claim 14, wherein there is provided means to position a reflective planar surface in the path of the radiation passing through said exit slit, said means to position said sample positions the sample for the light radiation from said exit slit to be transmitted through said sample to said reflective surface, said conical locus being positioned so that the ends of said fibers receive radiation reflected from said reflective surface with the axis of said conical locus perpendicular to said reflective surface.

17. Optical apparatus for analyzing a sample comprising a filament lamp having a filament, reflector means positioned to focus a real image of said filament along a side adjacent to said filament to form a composite image object with said filament in the form of a square an optical means for projecting light from said composite image object onto the sample, and means for detecting radiation from said sample.

18. Optical apparatus as recited in claim 17, wherein said means for detecting radiation from said sample includes a grating and means to project radiation from said sample onto said grating and optical sensing means to detect light dispersed by said grating.

19. Optical apparatus as recited in claim 17, wherein said optical sensing means detects light reflected from a reflective surface, and said optical means includes a first and second lens, said first lens being positioned to focus an image of said composite image object on said second lens and said second lens being positioned to focus an image of the radiation at said first lens on said reflective surface.

20. The optical apparatus of claim 19, wherein there is a means defining a circular aperture at said first lens whereby the radiation focused on said reflective surface is circular.

21. The optical apparatus of claim 19, wherein said reflective surface is a surface of the sample.

22. The optical apparatus of claim 19, wherein said reflective surface is positioned to receive light radiation transmitted through said sample.

23. Apparatus for irradiating a sample comprising a lamp having a linear filament, a support member rotatable with respect to said lamp about an axis passing through said lamp in a direction perpendicular to said filament, a reflector pivotally mounted on said first member arranged to focus an image of the filament of said lamp adjacent to said filament whereby the distance of the image of said filament from said filament can be adjusted by pivoting said reflector on said support member and the angular position of said lamp about said filament can be adjusted by rotating said support member about said axis.

24. Optical apparatus for analyzing a sample comprising a concave diffraction grating operable to disperse impinging light radiation into narrow bandwidth components, means to oscillate said diffraction grating, optical means for projecting light radiation on the oscillating grating, an entrance slit located between said optical means and the grating, an exit slit positioned to receive the light radiation dispersed by said grating, photosensing means for detecting light radiation that has passed through said exit slit, said means to oscillate said grating comprising an axle fixed to said grating, a pair of cam followers fixed to said axle, a pair of conjugate cams each having a surface continuously engaging a corresponding one of said cam followers, said grating being oscillated by the rotation of said conjugate cams with each acceleration and deceleration of the grating in one direction during its oscillation being effected by the action of one of the cam surfaces pushing on its corresponding cam follower and with each acceleration and deceleration of the grating in the other direction during its oscillation being effected by action of the other cam surface pushing on its corresponding cam follower.

* * * * *